(12) United States Patent
Ishige et al.

(10) Patent No.: US 6,187,996 B1
(45) Date of Patent: *Feb. 13, 2001

(54) PLANT PROMOTER COMPRISING A G-BOX ELEMENT, GCCACGTGCC OR GCCACGTGAG, AND AN APPLICATION THEREOF

(75) Inventors: Fumiharu Ishige, Toyonaka (JP); Nam-Hai Chua, Scarsdale, NY (US); Kenji Oeda, Takarazuka (JP)

(73) Assignees: Sumitomo Chemical Co., Ltd., Osaka (JP); The Rockefeller University, New York, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/680,116

(22) Filed: Jul. 15, 1996

(30) Foreign Application Priority Data

Jul. 14, 1995 (JP) ................................... 7-178730
Sep. 5, 1995 (JP) ................................... 7-227967
Jun. 7, 1996 (JP) ................................... 8-145492

(51) Int. Cl.$^7$ ............................ A01H 5/00; C12N 15/82; C12N 15/63; C07H 21/04
(52) U.S. Cl. ...................... 800/298; 432/320.1; 432/419; 536/24.1
(58) Field of Search .......................... 800/205, DIG. 43, 800/DIG. 46; 435/320.1, 419; 536/24.1

(56) References Cited

U.S. PATENT DOCUMENTS 5,625,136 * 4/1997 Koziel et al. .................. 800/205

FOREIGN PATENT DOCUMENTS 0 296 870 * 12/1988 (EP) .
0629697    12/1994 (EP) .
62-296882  * 5/1986 (JP) .
6205682     7/1994 (JP) .
WO 93/07278 * 4/1993 (WO) .
94 12015    * 6/1994 (WO) .

OTHER PUBLICATIONS

Salinas et al, The Plant Cell, vol. 4, pp. 1485–1493 (Dec. 1992).
Oeda et al, The EMBO Journal, vol. 10, No. 7, pp. 1793–1802 (1991).
Odell et al, Nature, vol. 313, pp. 810–812 (Feb. 28, 1985).*
Otten et al, Nature, vol. 321, pp. 669–674 (Jun. 12, 1986).*
Jefferson et al, The EMBO Journal, vol. 6, No. 13, pp. 3901–3907 (1987).*
Kay et al, Science, vol. 236, pp. 1299–1302 (Jun. 5, 1987).*
Sanders et al, Nucleic Acids Research, vol. 15, No. 4, pp. 1543–1558 (1987).*
Benfey et al, The EMBO Journal, vol. 8, No. 8, pp. 2195–2202 (1989).*
Ueda et al, The Plant Cell, vol. 1, pp. 217–227 (Feb. 1989).*
Van de Rhee et al, The Plant Cell, vol. 2, pp. 357–366 (Apr. 1990).*
Keil et al, The Plant Cell, vol. 2, pp. 61–70 (Jan. 1990).*
M. E. Williams et al., *The Plant Cell,* vol. 4, pp. 485–496 (Apr. 1992).
A. Galvanas et al., Genbank Database Accession No. L123533, XP002101289 (May 4, 1994).
R. Lafyatis et al., *Journal of Biological Chemistry,* vol. 265, No. 31, pp. 19128–19136 (Nov. 5, 1990).
Genbank Database Accession No. E07891, XP002101288, 1997.

* cited by examiner

Primary Examiner—Amy J. Nelson
(74) Attorney, Agent, or Firm—Birch, Stewart, Kolasch & Birch, LLP

(57) ABSTRACT

The present invention relates to a promoter functional in plant cells and plasmid that can regulate efficient expression of a gene of interest in plant cells. The promoter comprises a G-Box element, which enhances expression of an operably linked gene of interest in plants or plant cells. A further object of the invention is the plasmid pGbox10 or pGbox11, as well as plants or plant cells transformed with said plasmid.

22 Claims, 5 Drawing Sheets

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: both
      (D) TOPOLOGY: linear (ii) MOLECULE TYPE: other nucleic acid
      (A) DESCRIPTION: /desc = "plant promoter sequence"

(iv) ANTI-SENSE: NO (xi) SEQUENCE DESCRIPTION: SEQ ID NO:1:

GCCACGTGCC                                               10

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: both
      (D) TOPOLOGY: linear (ii) MOLECULE TYPE: other nucleic acid
      (A) DESCRIPTION: /desc = "plant promoter"

(xi) SEQUENCE DESCRIPTION: SEQ ID NO:2:

GCCACGTGAG                                                                10

(2) INFORMATION FOR SEQ ID NO:3:

(i) SEQUENCE CHARACTERISTICS:
        (A) LENGTH: 98 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:3:

ATCTCCACTG ACGTAAGGGA TGACGCACAA TCCCACTATC CTTCGCAAGA CCCTTCCTCT    60

ATATAAGGAA GTTCATTTCA TTTGGAGAGG ACACGCTG                            98

(2) INFORMATION FOR SEQ ID NO:4:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "-90 region + strand"

(xi) SEQUENCE DESCRIPTION: SEQ ID NO:4:

GATCATCTCC ACTGACGTAA GGGATGACGC ACAATCCCAC TATCCTTGGC AAGACCCTTC    60

CTCTATATAA GGAAGTTCAT TTCATTTGGA GAGGACACGC TG                      102

(2) INFORMATION FOR SEQ ID NO:5:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "-90 region - strand"

(xi) SEQUENCE DESCRIPTION: SEQ ID NO:5:

GATCCAGCGT GTCCTCTCCA AATGAAATGA ACTTCCTTAT ATAGAGGAAG GGTCTTGCGA    60

AGGATAGTGG GATTGTGCGT CATCCCTTAC GTCAGTGGAG AT                      102

(2) INFORMATION FOR SEQ ID NO:6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "tandem repeat of SEQ. ID. NO. 1"

(xi) SEQUENCE DESCRIPTION: SEQ ID NO:6:

AGCTTGCCAC GTGCCGCCAC GTGCCGCCAC GTGCCGCCAC GTGCCT                   46

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "tandem repeat of reverse
        complement of SEQ. ID. NO. 1"

(xi) SEQUENCE DESCRIPTION: SEQ ID NO:7:

CTAGAGGCAC GTGGCGGCAC GTGGCGGCAC GTGGCGGCAC GTGGCA                46

(2) INFORMATION FOR SEQ ID NO:8:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "tandem repeat of SEQ. ID. NO. 2"

(xi) SEQUENCE DESCRIPTION: SEQ ID NO:8:

AGCTTGCCAC GTGAGGCCAC GTGAGGCCAC GTGAGGCCAC GTGAGT                46

(2) INFORMATION FOR SEQ ID NO:9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "tandem repeat of reverse
            complement of SEQ. ID. NO. 2"

(xi) SEQUENCE DESCRIPTION: SEQ ID NO:9:

CTAGACTCAC GTGGCCTCAC GTGGCCTCAC GTGGCCTCAC GTGGCA                46

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "promoter region PCR primer"

(xi) SEQUENCE DESCRIPTION: SEQ ID NO:10:

CAGCTATGAC CATGATTACG CC                                          22

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "promoter region PCR primer"

(xi) SEQUENCE DESCRIPTION: SEQ ID NO:11:

CGCGCTTTCC CACCAACGCT GATC                                        24

PLANT PROMOTER COMPRISING A G-BOX ELEMENT, GCCACGTGCC OR GCCACGTGAG, AND AN APPLICATION THEREOF

FIELD OF INVENTION

The present invention relates to a plant promoter and an application thereof.

DESCRIPTION OF RELATED ART

For expression of an exogeneous structural gene of interest in a plant or plant cells, cauliflower mosaic virus 35S promoter (hereinafter referred to as "35S promoter") which consists of about 0.8 kb has been used, but the minimal region of the 35S promoter (e.g., −90 region of the 35S promoter which consists of 98 nucleotide bases (−90 to +8)) has not been satisfactory for practical expression of a gene of interest because of the low transcription activity of the region (Odell et al., Nature 313: 810–812 (1985), Jensen et al., Nature 321: 669–674 (1986), Jefferson et al., EMBO J. 6: 3901–3907 (1987), Kay et al., Science 236: 1299–1302 (1987), Sanderset et al., Nucl. Acid. Res. 4: 1543–1558 (1987), etc.), Benfey et al., EMBO J. 8: 2195–2202 (1989).

SUMMARY OF INVENTION

To facilitate efficient expression of an exogeneous structural gene of interest in a plant or plant cells, the present inventors have extensively studied and found that a compact specific nucleotide sequence can enhance the expression of a gene of interest when connected upstream to a promoter including the minimal region as described above.

An object of the present invention is to provide a promoter functional in plant cells, which contains the nucleotide sequence shown in SEQ ID NO:1 or SEQ ID NO:2.

In addition to the specific nucleotides shown in SEQ ID NO:1 or SEQ ID NO:2, the promoter may include additional nucleotide on the 5' and/or 3' end of the sequence.

Another object of the present invention is to provide a plasmid comprising a promoter functional in plant cells which contains the nucleotide sequence shown in SEQ ID NO:1 or SEQ ID NO:2, and a terminator functional in plant cells.

An object of the present invention is to provide a plasmid comprising a promoter functional in plant cells which contains the nucleotide sequence shown in SEQ ID NO:1 or SEQ ID NO:2, a structural gene of interest and a terminator functional in plant cells.

A further object of the invention is to provide a plasmid pGbox10 shown in FIG. 4 or pGbox11 shown in FIG. 5.

Further objects of the present invention are to provide a plant or plant cell expressing a structural gene of interest under the control of the promoter described above, and a plant harboring the plasmid described above.

Still further objects of the present invention are to provide a method for expressing in plant cells a structural gene of interest, wherein the expression is controlled by the promoter described above, and a method for constructing a plasmid, which comprises connecting the promoter of the present invention, a structural gene of interest and a terminator functional in plant cells in this order.

DESCRIPTION OF PREFERRED EMBODIMENT

Figure 1:
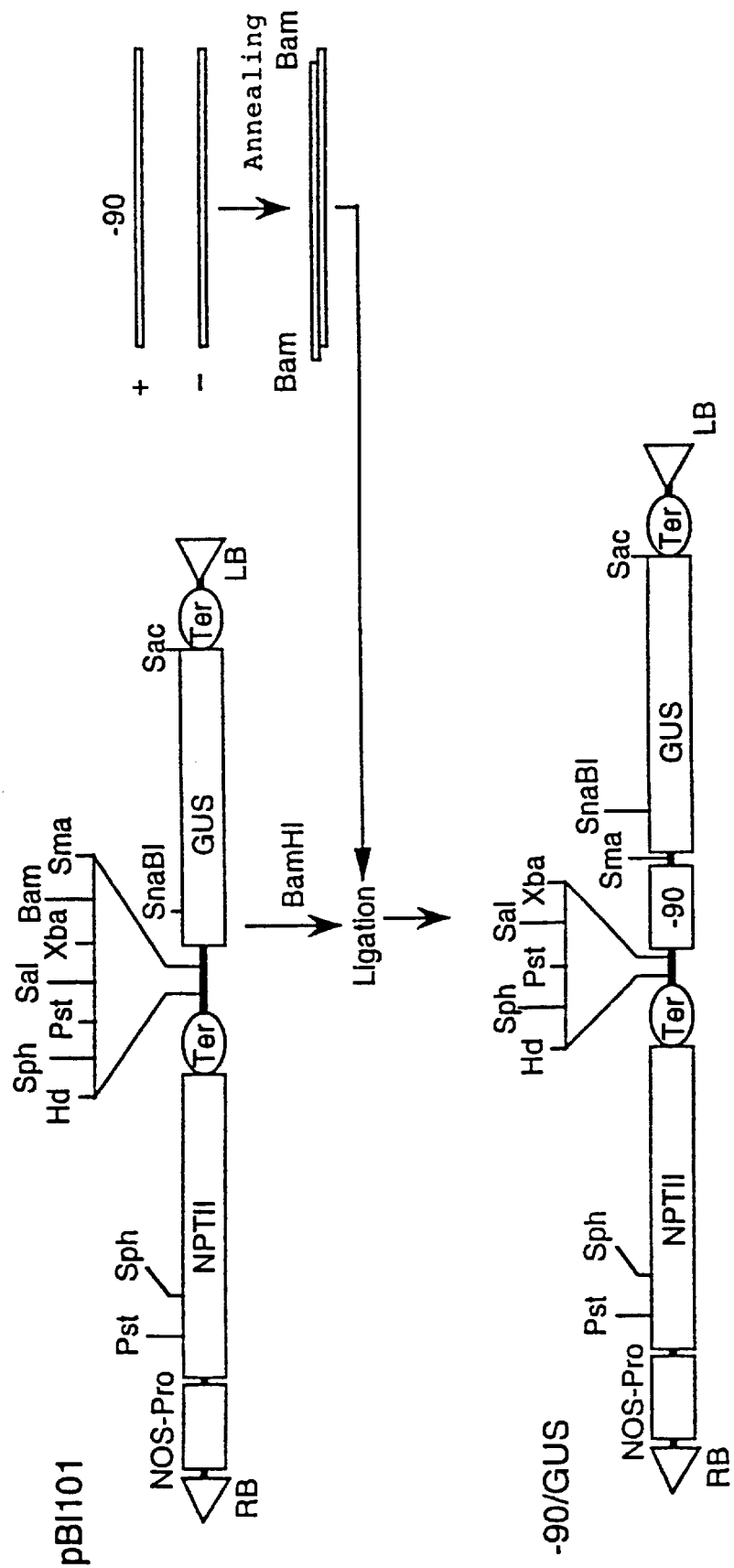
FIG. 1 shows the construction of plasmid −90/GUS from pBI101.

According to the present invention efficient expression of a gene of interest can be attained by the compact promoter.

The genetic engineering techniques to be used in the present invention follow standard procedures such as described in J. Sambrook, E. F., Frisch, T. Maniatis "Molecular Cloning, 2nd ed.", publ. Cold Spring Harbor Laboratory (1989), D. M. Glover, "DNA Cloning", publ. IRL (1985), and elsewhere.

First, description will be made on the promoter functional in plant cells, which contains the nucleotide sequence shown in Sequence ID No:1 or No:2. The promoter usually contains the sequence shown in SEQ ID NO:1 or SEQ. ID. NO:2, and preferably it contains multiple copies, particularly in the form of tandem repeats. The promoter preferably contains four or more such copies.

The nucleotide sequence shown in SEQ ID NO:1or SEQ ID NO:2 may be of either natural or synthetic origin.

Synthesis of the nucleotide sequence shown in SEQ ID NO:1 or SEQ ID NO:2 may be accomplished by standard DNA chemical synthetic techniques.

The present promoter usually contains a minimal element necessary for transcription initiation other than the nucleotide sequence shown in SEQ ID NO:1 or SEQ ID NO:2.

The element for transcription refers to a sequence region necessary for transcription initiation such as a transcription initiation site only, a transcription initiation site and TATA sequence, a transcription initiation site and CAAT sequence, alternatively a transcription initiation site and TATA sequence and CAAT sequence, etc.

A typical example of such a sequence region is provided by SEQ ID NO:3 and includes a sequence in which the 5'-terminus corresponds to a nucleotide sequence located at least about 30 nucleotides upstream of the transcription initiation site and in which the 3'-terminus sequence corresponds to the region from the transcription initiation site to the translation initiation site. The transcription activity of such a basic region is generally low. Specified examples of such regions include the 98 nucleotide base region of the 35S promoter which includes the transcription initiation site (+8 to −90) (hereinafter referred to as the "−90 region"), the −204 to +8 region of the tomato gene encoding the small subunit of the Ribulose-1,5-diphosphate carboxylase-oxidase (rbcS-3A) (Plant Cell 1: 217–227 (1989)), the −287 to +29 region of the PR1a gene promoter (Plant Cell 2: 357–366 (1990)), and the −195 to +32 region of the potato protease inhibitor gene (PI-II) (Plant Cell 2: 61–70 (1990)). The regions described above that contain a minimal element necessary for transcription initiation are usually utilized by inserting them downstream of the nucleotide sequence shown in SEQ ID NO:1 or SEQ ID NO:2.

The nucleotide sequence shown in SEQ ID NO:1 or SEQ ID NO:2 and the sequence containing a minimal element for transcription initiation may be prepared by restriction enzyme digestion of genomic DNA whose sequence is known, or by Polymerase Chain Reaction (PCR) amplification of a region of a DNA nucleotide containing SEQ ID NO:1 or SEQ ID NO:2, or the sequence containing a minimal element for transcription initiation using genomic DNA as a template and appropriate oligonucleotides as primers, or by DNA chemical synthesis.

When the −90 region of the 35S promoter is utilized, the promoter of the present invention may be constructed by synthesizing and annealing oligonucleotides representing the +strand (refer to Sequence No:4) and the −strand (refer to SEQ ID NO:5 of the −90 region.

With respect to the 35S promoter, a deletion promoter which is shorter than the −90 region may be obtained, and is usually constructed by digestion with restriction enzymes, by PCR amplification using genomic DNA as a template and oligonucleotide primers having sequences appropriate to amplify the deletion promoter region, or by DNA chemical synthesis methods.

The terminator functional in plant cells to be used in the present invention includes, for example, plant-derived terminators such as the terminator from the T-DNA-derived nopaline synthase gene (NOS), or virus-derived terminators usually used in plant genetic engineering techniques, such as the terminators from the Garlic virus GV1 and GV2 genes.

The plasmid of the present invention comprises a promoter functional in plant cells, which contains the nucleotide sequence shown in SEQ ID NO:1 or NO:2, and a terminator functional in plant cells.

The plasmid of the present invention is preferably constructed so as to contain at least one cloning site upstream of the terminator and downstream of the promoter to accommodate the desired structural gene. More preferably the plasmid is constructed in such a way as to contain multiple cloning sites. The term "cloning site" here refers to a region of DNA which can be recognized and digested by restriction enzymes usually utilized in genetic engineering procedures.

Figure 4:
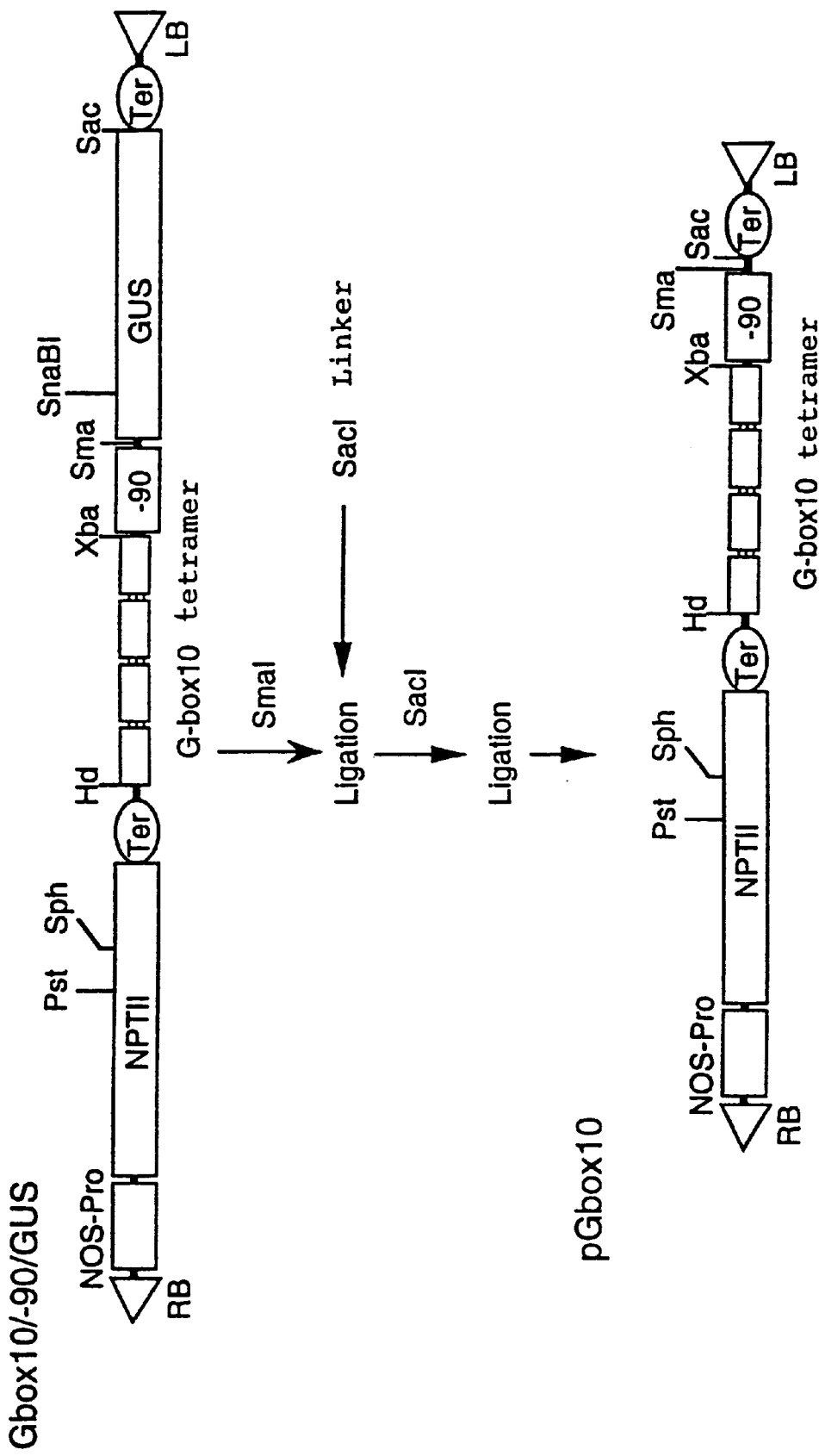
FIG. 4 shows the construction of pGbox10 from the plasmid Gbox10/−90/GUS.
Figure 5:
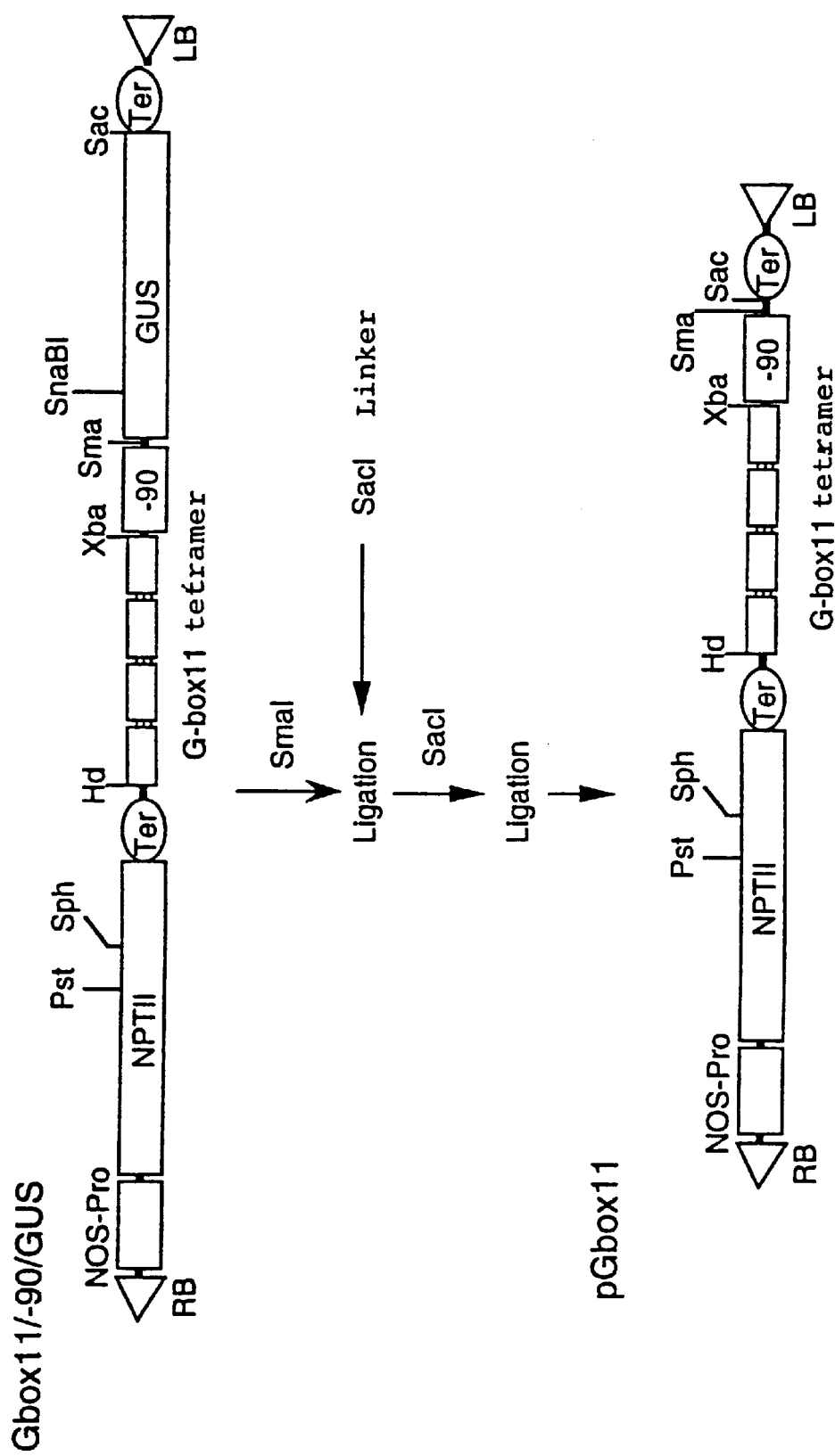
FIG. 5 shows the construction of pGbox11 from the plasmid Gbox11/−90/GUS.

One example of such a plasmid containing cloning sites is the plasmid pGbox10 shown in FIG. 4 or the plasmid pGbox11 shown in FIG. 5.

Examples of useful exogenous structural genes which may be expressed under the control of the present plasmid are plant defense genes such as the phenylalanine ammonia lyase gene (PAL), the chalcone synthetase gene (CHS), the chitinase gene (CHT), the lysozyme gene, the PR protein gene, etc., disease resistance genes such as Pto, and genes which increase the resistance against bacteria, fungi, viruses and insects in all plant tissues such as the virus coat protein gene, BT (*Bacillus thuringiensis*) toxin protein gene, etc.

Other useful genes include those which increase the protein content of feed crops such as genes encoding storage proteins, the soybean glycinin gene, and the β-conglycinin gene, etc., genes which increase the methionine and lysine content of feed crops, such as the Brazil nut 2S albumin gene, the 10 kDa or 15 kDa protein genes from maize and rice, etc. and genes which increase the biotin content of feed crops such as the bacterial genes from *Escherichia coli*, etc. which encode the bioA, bioB, bioC, bioD, bioF, and bioH enzymes involved in the synthesis of biotin.

Other useful genes include those which improve the quality of lipids by providing stability to oxidation, decreasing the phospholipid content and increasing the oleic acid and linoleic acid content such as the stearoyl-ACP-desaturase, acyl-ACP-thioesterase, and 3-phosphate acyltransferase genes, genes which increase the resistance to low temperatures by increasing the proportion of unsaturated fatty acids such as the acetyltransferase gene, and genes which make possible the generation of herbicide-resistant crops such as by the expression of the gene encoding L-phosphinothricin acetyltransferase, 5-enolpyrvil-3-phosphosikimate synthase or of other genes related to herbicide resistance.

After the plants of the present invention are grown, the whole plants or parts of the plants can be harvested and sold. Components of the plants, especially components containing expression products of the structural gene of interest, can be separated from, extracted from and/or concentrated from the plants by conventional techniques. Likewise, plant cells can be harvested and sold as a commercial product per se (such as a food source of food additives) and/or components of the plant cells, in particular components containing expression products of the structural genes of interest, can be separated from, extracted from and/or concentrated from the plant cells from the plant cells by conventional techniques.

The plasmid of the present invention may be constructed, for example, by the following method. The promoter functional in plant cells, which contains the nucleotide sequence shown in SEQ ID NO:1 or SEQ ID NO:2, is inserted into the multicloning site of the plasmid containing the terminator functional in plant cells such as pBI101 (Clontech Inc.; Jefferson et al., EMBO J. 6: 3901–3907 (1987)).

Furthermore an exogenous marker gene such as β-glucuronidase can be excised and replaced with a desired structural gene as necessary. Another possible method is to use a binary vector such as pBIN19 (Nuc. Acid. Res. 12: 8711–8721 (1984)) and insert the promoter, the desired structural gene if necessary, and the terminator to be used in the present invention, in that order, into the multicloning site.

As for the methods for introducing the plasmid into plant cells, there are conventional methods such as the Agrobacterium infection method (i.e. infection of plant tissue with the soil bacteria Agrobacterium), electric-based introduction methods (electric-based method of introduction into protoplasts: electroporation), or direct introduction by a particle gun (direct introduction into plant tissues or cultured cells: particle gun method). Plant cells harboring the plasmid of the present invention may be obtained by the conventional plant tissue culture techniques described in, e.g. S. B. Gelvin, R. A. Schilperoot and D. P. S. Verma, Plant Molecular Biology/Manual, Kluwer Academic Publishers press, 1988 and subsequently plants or their parts derived from these plant cells may be obtained by regeneration according to the protocols described therein.

Moreover, the method described herein may be applied for the plant species which include monocots such as rice, maize, barley, wheat, and onion, dicots such as the members of the Leguminosae, i.e. soybeans, peas, kidney beans, alfalfa, members of the Solanaceae such as tobacco, tomato, and potato, members of the Cruciferae such as cabbage, rapeseed, mustard plant, members of the Cucurbitaceae (gourd family) such as melon, pumpkin, cucumbers, members of the Ammiaceae such as carrot and celery, and members of the Compositae such as lettuce.

According to the present invention, plant cells (transformed plant cells) and plants (transformed plants) expressing a structural gene of interest can be obtained efficiently by using the compact promoter or plasmid of the present invention.

EXAMPLES

The present invention will be further illustrated in more detail by the following examples.

Example 1

Figure 2:
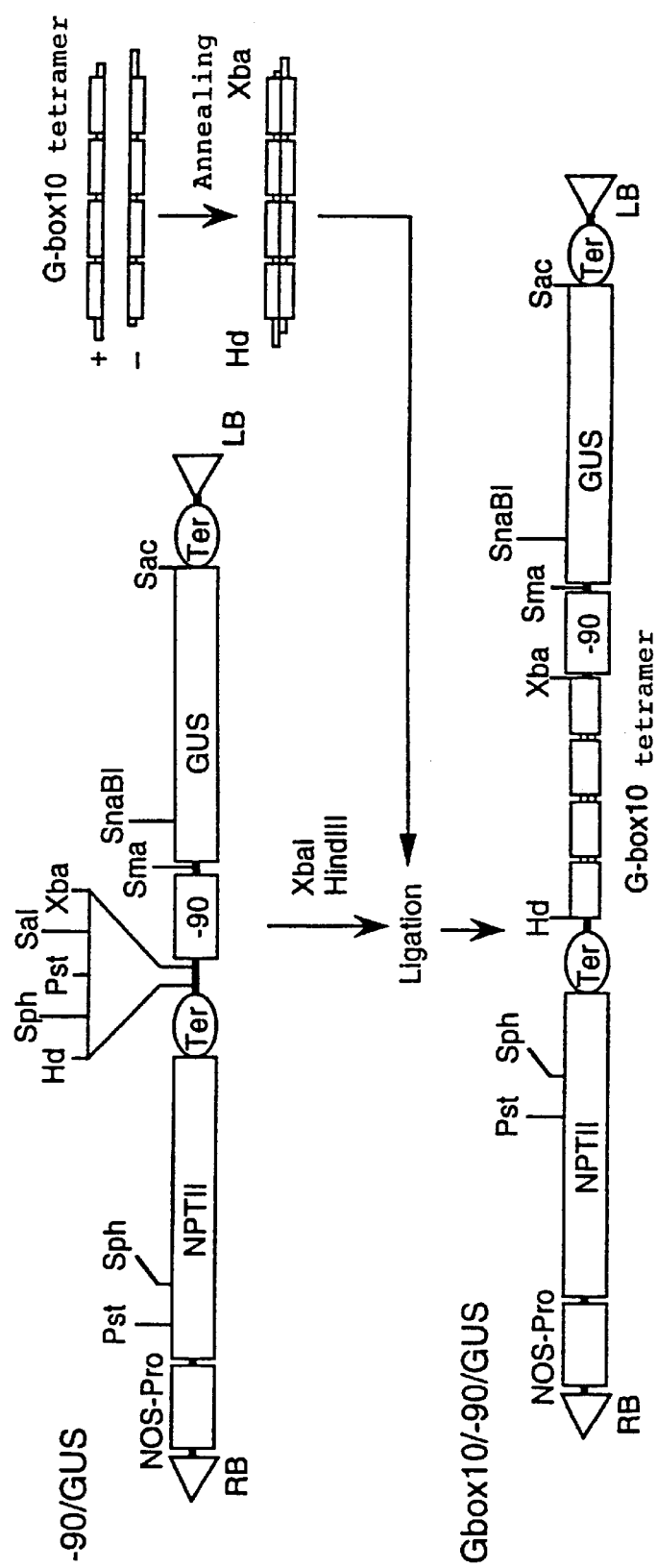
FIG. 2 shows the construction of the plasmid Gbox10/−90/GUS from plasmid −90/GUS.
Figure 3:
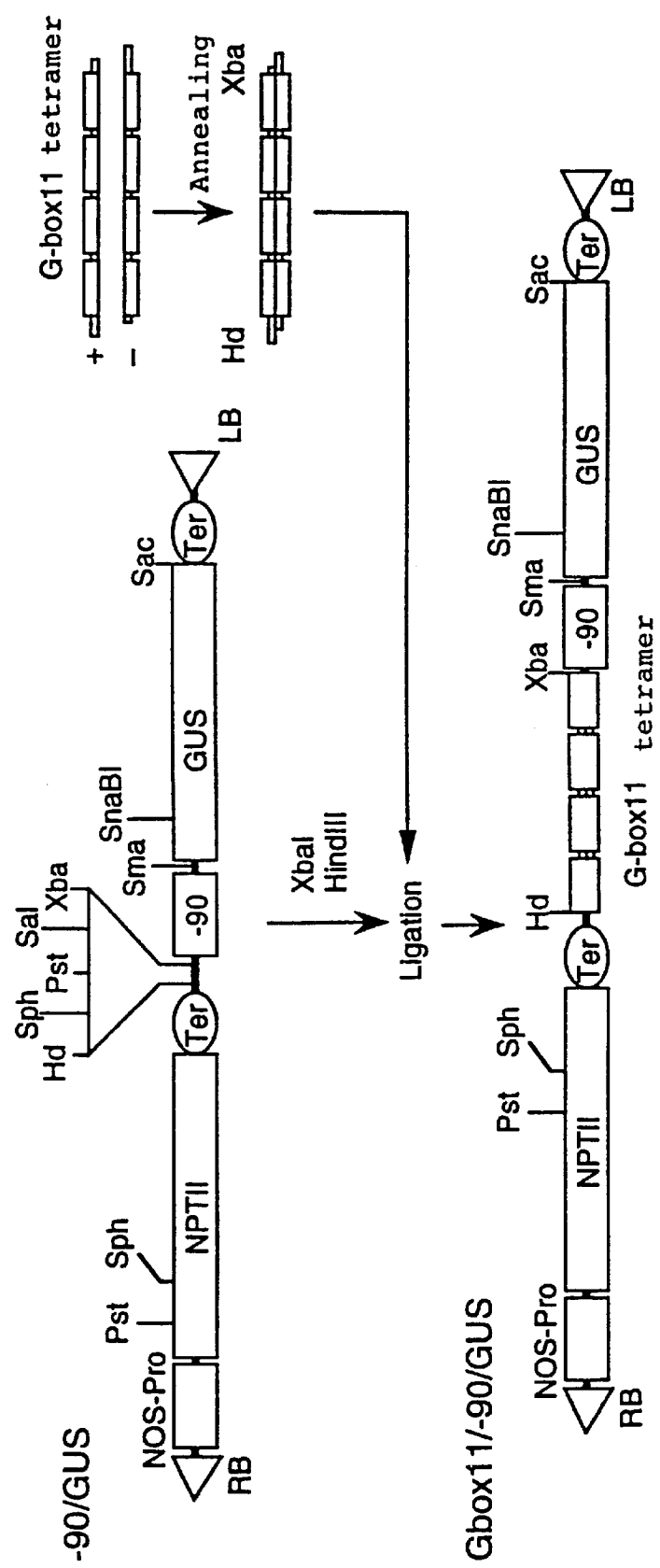
FIG. 3 shows the construction of the plasmid Gbox11/−90/GUS from plasmid −90/GUS.

Construction of GUS Expression Plasmids Gbox10/−90/GUS. Gbox11/−90/GUS and −90/GUS The plasmid −90/GUS was constructed by inserting the −90 region prepared by DNA chemical synthesis into the multicloning site upstream of the GUS gene contained within the commercially available plasmid pBI101 (Clontech Inc.; Jefferson et al., EMBO J. 6: 3901–3907 (1987)) which also contains a terminator functional in plant cells. The plasmid Gbox10/-90/GUS and plasmid Gbox11/-90/GUS were further constructed by inserting upstream of the -90 region of -90/GUS a multimer containing 4 tandem repeats of the nucleotide sequence shown in SEQ ID NO:1 or SEQ ID NO:2, respectively. The method of construction is explained in detail below (refer to FIGS. 1, 2 and 3).

Step 1: Synthesis and Purification of Complementary Oligonucleotides Containing 4 Tandem Repeats of G-box10 or G-box11 and Complementary Oligonucleotides Containing the -90 Region Two complementary oligonucleotides (+strand and −strand, 46 bases each, refer to SEQ ID NO:6, 7, 8 and 9) containing a multimer consisting of tandem repeats of the oligonucleotide sequence shown in SEQ ID NO:1 or NO:2 and having a HindIII restriction site at the 5'terminus and XbaI site at the 3'terminus when annealed were chemically synthesized.

Further two complementary oligonucleotides (+strand and −strand, 102 bases each, refer to SEQ ID NO:4 and SEQ ID NO:5) containing the -90 region which includes the minimal elements necessary for transcription initiation and BamHI restriction sites at both termini when annealed were chemically synthesized.

These chemically synthesized oligonucleotides were deprotected with ammonia treatment (55° C., 5 hr) and subsequently purified by reverse-phase HPLC (YMC GEL ODS S-5). The solvent used in purification was 0.1 M triethylamine (TEAA) and the oligonucleotides were extracted using a concentration gradient of 5–100% methyl cyanide ($CH_3CN$). The extracted oligonucleotides were recovered, the residue dried, redissolved in 80% acetic acid (3 ml) for 20 min and subsequently dried again. The dried residue was redissolved in distilled water (3 ml) and redried, and this procedure was repeated for a total of three times before the sample was finally dissolved in 100 $\mu$l of TE (10 mM Tris-HCl pH 8.0, 1 mM EDTA). The oligonucleotide sample thus obtained was further purified by electrophoresis with a 5% polyacrylamide gel (80 V, 1 hr). The pair of complementary oligonucleotides containing the multimer consisting of 4 tandem repeats of the nucleotide sequence shown in SEQ ID NO:1 or SEQ ID NO:2 (42 bases each) as well as the pair of complementary oligonucleotides containing the -90 region (102 bases each) were each extracted from the polyacrylamide gel and recovered by electrophoretic transfer (180 V, 40 mins.) out of the gel in dialysis tubing (SPECTRA/POR, molecularporous membrane tubing MW 3500).

Step 2: Annealing of Complementary Strands 0.5 $\mu$g of a pair of complementary oligonucleotides containing the multimer consisting of 4 tandem repeats of the nucleotide sequence shown in SEQ ID NO:1 or NO:2, and a pair of complementary oligonucleotides containing the -90 region (102 bases) were heated to 100° C. for 3 min in 10 $\mu$l aqueous solution, transferred to a 65° C. water bath, allowed to slowly return to room temperature and finally chilled quickly in ice water. By this procedure a DNA fragment containing a multimer consisting of 4 tandem repeats of the nucleotide sequence shown in SEQ ID NO:1 or SEQ ID NO:2, and a DNA fragment containing the -90 region (102 bases) were prepared.

Step 3: Construction of the -90/GUS Plasmid

2 $\mu$g of pBI101 were digested with 10 units of BamHI and 0.1 $\mu$g of the -90 region (102 bases) prepared in step 2 and 0.5 $\mu$g of the BamHI-digested pBI101 were mixed and ligated using T4 DNA ligase (DNA ligation kit, Takara Shuzo Ltd.). This mixture was used to transform the *E. coli* strain HB101 (Takara Shuzo Ltd.) according to the protocol of Cohen et al. (Proc. Natl. Acad. Sci. USA, 69: 2110–2114 (1972)). From the resistant colonies grown up on LB agar plates containing 50 $\mu$g/ml kanamycin plasmid DNAs were extracted by the alkaline-SDS method and their structures were analyzed by restriction enzyme digestion. Isolated plasmids which yielded approx. 100 bp DNA fragment upon digestion with SmaI and XbaI were selected. The sequences of the DNA inserted in these selected plasmids were determined by the dideoxy method (Sanger et al., Proc. NAtl. Acad. Sci., USA, 74: 5463 (1977)) and clones in which the -90 region had been inserted in the proper orientation were chosen where the proper orientation means the same orientation of the -90 region as is found in the 35S promoter. Thus the -90/GUS plasmid was constructed (see FIG. 1).

Step 4: Construction of the Gbox10/-90/GUS Plasmid and Gbox11/-90/GUS Plasmid

2 $\mu$g of the -90/GUS plasmid prepared in step 3 were digested with 10 units of XbaI and HindIII (37° C., 2 hrs.), and the digestion products were fractionated by electrophoresis in 0.8% low melting-point agarose (80 V, 1.5 hr). The HindIII-XbaI fragment was recovered using a centrifugation tube with a DNA recovery filter (Takara Shuzo Ltd.) and purified.

0.1 $\mu$g of the DNA fragment prepared in Step 2 containing multimer consisting of 4 tandem repeats of the nucleotide sequence shown in SEQ ID NO:1 or SEQ ID NO:2 respectively, and 0.5 $\mu$g of the HindIII-XbaI-digested -90/GUS plasmid were mixed and ligated using T4 DNA ligase (DNA ligation kit, Takara Shuzo Ltd.). This mixture was used to transform the *E. coli* strain HB101 (Takara Shuzo Ltd.) according to the protocol of Cohen et al. (Proc. Natl. Acad. Sci. USA, 69: 2110–2114 (1972)).

From the resistant colonies grown up on LB agar plates containing 50 $\mu$g/ml kanamycin plasmid DNAs were extracted by the alkaline-SDS method and their structures were analyzed by restriction enzyme digestion. Isolated plasmids which yielded approx. 50 bp DNA fragments upon digestion with HindIII and XbaI were selected. The structures of the plasmids were confirmed by the dideoxy method (Sanger et al., Proc. Natl. Acad. Sci., USA, 74: 5463 (1977)), and the sequences of the DNA inserts were determined. Thus, the Gbox10/-90/GUS plasmid and Gbox11/-90/GUS plasmid were constructed respectively (see FIGS. 2 and 3).

Example 2

Construction of pGbox10 and pGbox11

2 $\mu$g of the plasmid Gbox10/-90/GUS and plasmid Gbox11/-90/GUS were each digested with 10 units of SmaI (37° C., 2 hrs.) respectively. 0.1 $\mu$g of the digestion product was mixed with 0.05 $\mu$g of commercially available SacI linkers (5'-CGAGCTCG-3') (Takara Shuzo Ltd.) and ligated using T4 DNA ligase (DNA ligation kit, Takara Shuzo Ltd.). The ligation products were subsequently digested with 10 units of Sac1, religated with T4 DNA ligase (DNA ligation kit (Takara Shuzo)) and used to transform the *E. coli* strain HB101 (Takara Shuzo) according to the method of Cohen et al. (Proc. Natl. Acad. Sci. USA. 69: 2110–2114 (1972)). From the resistant colonies grown up on LB agar plates containing 50 $\mu$g/ml kanamycin plasmid DNAs were extracted by the alkaline-SDS method and their structures were analyzed by restriction enzyme digestion. Isolated plasmids were subjected to SmaI and SacI digestion and single linear DNA fragments were selected. Thus the plasmid pGbox10 and plasmid pGbox11 were constructed respectively(see also FIGS. 4 and 5).

Example 3

Preparation of Plasmid DNA for Gene Introduction

The plasmids Gbox10/−90/GUS, Gbox11/−90/Gus, and −90/GUS prepared in Example 1 were further purified by cesium chloride density gradient centrifugation technique respectively. These DNA plasmids were purified by adding 1 g of cesium chloride and 80 µl of 10 mg/ml ethidium bromide per 1 ml of DNA solution. Sealing the resulting solution in centrifuge tubes (Quick-Seal, Beckman Co.) and subjecting the solution to centrifugation in an NVT65 rotor at 60,000 rpm for 24 hr, yielded the purified plasmid.

Example 4

Generation of Transformed Tobacco Plant by Indirect Introduction Method

Each purified plasmid described in Example 3 was introduced by heat treatment (37° C., 5 mins.) into Agrobacterium (Agrobacterium tumefaciens LBA4404; streptomycin resistant, rifampicin resistant; Hoekma et al., Nature 303: 179–180 (1983)) treated with 20 mM $CaCl_2$ to make them competent. Transformants were obtained by utilizing the kanamycin resistance conferred by the plasmid NPTII gene (Trien-Cuot et al., Gene 23: 331–341 (1983)) and being selected on L agar plates containing 300 µg/ml streptomycin, 100 µg/ml rifampicin and 100 µg/ml kanamycin.

The Agrobacterium transformants thus obtained were cultured at 20° C. for a day in L broth media containing 300 µg/ml streptomycin, 100 µg/ml rifampicin and 100 µg/ml kanamycin and this bacterial suspension was then used to infect a disc of tobacco plant according to the standard protocol described in S. B. Gelvin, R. A. Schilperoot and D. P. S. Verma, Plant Molecular Biology Manual, publ. Kluwer Academic Publishers, 1988.

The infected tobacco leaf discs (SR-1) were cultured for 4 days in MS-NB agar media and then transferred to MS-NB agar media containing 500 µg/ml cefotaxime to kill the Agrobacteria. 11 days later the leaf discs were transferred to MS-NB agar media containing 500 µg/ml cefotaxime and 100 µg/ml kanamycin thus the selection of transformed plants was initiated. Approximately 4 weeks later young plants from which green stems and leaves had developed were separated from the leaf disc and further cultured on MS agar media containing 500 µg/ml cefotaxime and 50 µg/ml kanamycin, after which young plants giving rise to roots were selected. The selected young plants were transferred to soil and cultivated in a greenhouse to produce transformed plants.

Example 5

Generation of Transformed Carrot by Indirect Introduction

G-box10/−90/GUS purified in Example 3 was introduced into Agrobacterium tumefaciens LBA4404 according to the method described in Example 4 and the obtained Agrobacterium was infected to hypocotyl of a carrot species, Nantes Scarlet.

The infected carrot hypocotyl was placed on LS-D agar medium containing 500 µg/ml cefotaxime. Selection of the transformed plant was initiated after 10 days later by placing the plant to LS-D agar media containing 100 µg/ml cefotaxime and 50 µg/ml kanamycin. The generated callus after one month was transferred to a LS-D agar media containing 100 µg/ml cefotaxime and 50 µg/ml kanamycin repeatedly every four weeks. The callus selected after 2 months was transferred to LS agar media and a whole plant was regenerated by way of adventitive embryo.

Example 6

Production of Transformed Plant by Direct Introduction

G-box10/−90/GUS purified as described in Example 3 was introduced into immature embryo of rice, Notohikari with a particle gun (Reebock company) according to a method described in Shimada, T., et al., Bull.RIAR, Ishikawa Agr. Coll.4:1–8 (1995) or Ko Shimamoto and Kiyotaka Okada, Experimental Protocol of model plant, Rice and Arabidopsis, Syujyun-sya, 1996 (ISBN4-87962-157-9 C3345). After sterilized seeds were cultured for 7 to 10 days in LS-D2 media, the embryo was picked up and placed on LS-D2 agar media with its scutellum organ upside. 10 µg of either G-box10/−90/GUS, −90/GUS, or pBI121 (35S/GUS) as a control, and pDM302 containing equimolar amount of bialaphos resistance gene (J. Cao et al., Plant Cell Rep. 11:586–591, 1992) were coated on 3 mg of a gold particle (avarage diameter 1 µm). Two shots were injected into rice embryos with each shot containing 0.2 mg of gold particle (1 µg DNA, Injection pressure 150–200 $kg/cm^2$, at 70 mmHg). Two days after the introduction resulting embryos were transferred to LS-D2 agar media containing 4 mg/ml of bialaphos to select herbicide resistant cells. The thus obtained herbicide resistant callus were transferred to culturing media for redifferentiation and regenerated adventitious embryos or small plants were transferred to LS agar media containing 4 mg/ml of bialaphos to grow the herbicide resistant plants.

Example 7

Confirmation of Insertion of the Introduced Gene in Transformed Plants

1. Preparation of Genomic DNA from Transformed Plants

Genomic DNA was isolated from transformed plants according to the CTAB method described in Hirofumi Utiyama, Plant Gene Engineering Manual for Producing Transgenic Plants, Kodansha Scientific; page 71–74, ISBN4-06-153513-7 c3045.

A tobacco leaf disc (approximately 0.5 g) from each transformed plant obtained in Examples 4, 5 and 6 was pulverized using a homogenizer in an Eppendorf tube to which was subsequently added 0.5 ml of 2×CTAB (2% acetyltrimethyl ammonium bromide, 1% polyvinylpyrrolidone (PVP)) pre-warmed to 65° C. and this mixture was incubated at 65° C. for 5 min. 0.5 ml of chloroform/isoamylalcohol (24:1) was then added and the sample was gently mixed for 5 min. The sample was separated by centrifugation at 12,000 rpm (10,000×g) for 10 minutes, 0.5 ml of isopropyl alcohol was added to the upper phase and the sample was mixed. After centrifugation at 12,000 rpm (10,000×g) for 15 min the precipitate obtained was dissolved in 200 µl TE (10 mM Tris-HCl pH 8.0, 1 mM EDTA). RNase was added so as to obtain a final concentration of 10 µg/ml and the sample incubated for 30 min at 37° C. to degrade RNAs. Following RNase treatment a mixture of equilibrated phenol/chloroform/isoamylalcohol (25:24:1) was added, the sample thoroughly mixed and the upper phase was collected. ⅒th volume of 3 M sodium acetate (pH 5.2) and 2.5 volumes of ethanol were added, the sample was thoroughly mixed and approximately 5 μg of genomic DNA was obtained by centrifugation at 12,000 rpm (10,000×g) for 5 min.

2. Confirmation of Gene Introduction by the PCR Method

Using 50 μg of the genomic DNA obtained above as a template and synthetic DNA with the nucleotide sequences shown in SEQ ID NO:10 and SEQ ID NO:11 as primers, the promoter region was amplified using the PCR method (30 reaction cycles of 94° C. for 1 min, 55° C. for 2 min and 72° C. for 3 min). The PCR product obtained was analyzed by electrophoresis in 12% polyacrylamide gel (PAGE) (80 V, 1 hr.). By this procedure a DNA fragment corresponding to the promoter region (approx. 250 bp for Gbox10/−90/GUS and Gbox11/−90/GUS or 290 bp for −90/GUS) with the expected size was obtained.

Example 8

Self-fertilization and Development of Genetically Homologous Line from Transformed Plant The transformed young plant generated in Example 4 was transferred to soil and cultivated to give rise to a transformed plant. At the time of anthesis (flowering) the plants were self-pollinated and seeds were obtained from the mature flowers. The seeds were sterilized for 5 min in 1% sodium hypochlorite, after which they were inoculated onto MS agar media containing 100 μg/ml kanamycin. Clones whose seeds all sprouted and developed after inoculation were selected.

Example 9

GUS Gene Expression in Transformed Tobacco Plant Tissues

GUS staining of the seeds, leaves and roots of the transformed tobacco plant obtained in Example 8 (containing either the plasmid, Gbox10/−90/GUS or Gbox11/−90/GUS or the plasmid −90/GUS or pBI121 as a control) was carried out according to the methods described in Hirofumi Uchiyama, Plant Gene Engineering Manual for Producing Transgenic Plant, Kodansha Scientific; page 68–70, 1990, ISBN4-06-153513-7 c3045 and Jefferson, Plant Mol. Biol. Rep. 5: 387–405 (1987). Seeds of the respective transformed tobacco plants were sterilized in 1% sodium hypochlorite and transferred to MS agar media containing 100 μg/ml kanamycin and allowed to develop seedlings for approximately two weeks.

Activity staining was performed using 5-bromo-4-chloro-3-indole-β-D-glucuronic acid (X-Gluc) as a substrate and measuring the amount of the precipitated blue pigment (indigotin).

Staining: Seeds from 40 individuals of each plant sample (transformed tobacco plants containing the plasmid, Gbox10/−90/GUS, Gvox11/−90/GUS, −90/GUS or pBI121 for comparison, or an untreated tobacco variety, SR-1 as a control) were sliced with a scalpel and immersed overnight at 37° C. in GUS staining solution (1 mM X-Gluc, 0.5 mM K₃[Fe(CN)₆], 0.5 mM K₃[Fe(CN)₆], 0.3% Triton X-100). Plant tissues were then transferred to ethanol, destained by several washes in ethanol and the amount of remaining blue pigment precipitate measured. The results of the GUS staining assay of seeds, young leaves and roots of transformed plants containing the plasmid of the present invention, Gbox10/−90/GUS, Gbox11/−90/GUS, −90/GUS or pBI121 for comparison, or the untreated tobacco variety SR-1 as a control are shown in Tables 1–3.

TABLE 1

GUS staining in seeds

| | Degree of staining (%) | | | |
|---|---|---|---|---|
| Plasmid | A | B | C | none |
| SR-1 (control) | 0 | 0 | 0 | 100 |
| −90/GUS (Comparison 1) | 0 | 0 | 75 | 25 |
| Gbox10/−90/GUS (present plasmid) | 83 | 0 | 17 | 0 |
| Gbox11/−90/GUS (present plasmid) | 3 | 59 | 31 | 7 |
| pBI121 (35S/GUS) (Comparison 2) | 30 | 50 | 10 | 10 |

A: the entire seed is darkly stained
B: an area of dark staining emerging around the base (primordium) of the root in the seed
C: the base of the root in the seed is stained
none: no staining

TABLE 2

GUS staining in leaves

| | Degree of staining (%) | | | |
|---|---|---|---|---|
| Plasmid | dark | moderate | light | none |
| SR-1 (control) | 0 | 0 | 0 | 100 |
| −90/GUS (Comparison 1) | 0 | 0 | 0 | 100 |
| Gbox10/−90/GUS (present plasmid) | 100 | 0 | 0 | 0 |
| Gbox11/−90/GUS (present plasmid) | 70 | 24 | 3 | 3 |
| pBI121 (35S/GUS) (Comparison 2) | 67 | 11 | 11 | 11 |

"dark", "moderate", "light", and "none" refer to the degree of staining

TABLE 3

GUS staining in roots

| | Degree of staining (%) | | | |
|---|---|---|---|---|
| Plasmid | dark | moderate | light | none |
| SR-1 (control) | 0 | 0 | 0 | 100 |
| −90/GUS (Comparison 1) | 0 | 4 | 22 | 74 |
| Gbox10/−90/GUS (present plasmid) | 100 | 0 | 0 | 0 |
| Gbox11/−90/GUS (present plasmid) | 53 | 27 | 10 | 10 |
| pBI121 (35S/GUS) (Comparison 2) | 75 | 0 | 0 | 25 |

"dark", "moderate", "light", and "none" refer to the degree of staining

In the non-transformed (untreated) tobacco variety SR-1 none of the tissues exhibited staining. In plants transformed with −90/GUS plasmid containing the minimal necessary elements for transcription initiation from the 35S promoter light staining was seen in the base (primordium) of the root. In plants transformed with the plasmid of the present invention Gbox10/−90/GUS and Gbox11/−90/GUS virtually all specimens exhibited heavy staining in the seeds, leaves and roots. Particularly very heavy and uniform staining was observed in the plant subjected to Gbox10/−90/GUS.

Example 10

GUS Gene Expression in Transformed Carrot

GUS staining was conducted with leaves of the transformed carrot plant (containing the plasmid of the present invention, Gbox10/−90/GUS and pBI121 as a control) in which the presence of introduced gene was confirmed in Example 7 according to the method as described in Example 9. No staining was observed for the leaves of untreated untransformed carrot. Heavy staining was observed for the leaves of most of the test specimen of the plant transformed with the plasmid of the present invention, Gbox10/–90/GUS.

Example 11

GUS Gene Expression in Transformed Rice

Expression of GUS gene in the leaves of the small transformed rice plant (height 10 cm) prepared in Example 6 or the gene was confirmed in Example 7 was examined according to the GUS staining method as described in Example 9. While little staining was observed in the leaves of untreated untransformed rice, strong GUS activity was observed in the leaves of the plant transformed with Gbox10/–90/GUS.

The DNA length of the gene casette comprising a promoter functional in plant cells, a structural gene of interest and a terminator functional in plant cells contained in the present plasmids Gbox10/–90/GUS and Gbox11/–90/GUS is 2,300 bp (140 bp for the promoter), while that of pBI121 (35S/GUS) is 2,960 bp (800 bp for the promoter), and the gene casette to be introduced became about 22% shorter (83% for the promoter).

The composition of the media used in the Examples are described below.

1. MS Agar Media 34.7 g of MURASHIGE AND SKOOG (Flow Laboratories) is dissolved in 1 liter of distilled water and the pH of the solution was adjusted to pH 5.8 with 1 M KOH. 8 g of agar are added and the mixture is sterilized by autoclaving.

2. MS-NB Agar Media 0.1 mg/ml of 1-naphthalene acetic acid (NAA) and 0.1 mg/ml 6-benzylaminopterin (BA) are added to MS agar media.

3. LS Media 34.7 g of MARUSHIGE AND SKOOG (Flow Laboratories) and 30 g of sucrose were dissolved in 1 liter of distilled water and the pH of the resulting solution was adjusted to pH 5.8 by 1 M KOH and sterilized by autoclaving.

4. L Agar Media

Media obtained by adding agar 8 g/L to LS media.

5. LS-D Agar Media

Media obtained by adding 1.0 mg/L of 2,4-dichlorophenoxyacetic acid to LS agar media.

6. LS-D2 Agar Media

Media obtained by adding 2.0 mg/L of 2,4-dichlorophenoxyacetic acid to LS agar media.

7. L Broth Media 10 g of Bacto-tryptone (Difco), 5 g of Bacto yeast extract (Difco), and 10 g of NaCl are dissolved in 1 liter of distilled water, the pH is adjusted to 7.0 with 5 M NaOH and the media is sterilized by autoclaving.

According to the present invention efficient expression of a gene of interest can be attained.

What is claimed is:

1. A recombinant promoter which is functional in plant cells, wherein said promoter comprises at least one enhancer element comprising the nucleotide sequence of SEQ ID NO:1 or SEQ ID NO:2.

2. The promoter according to claim 1, which comprises a plurality of said enhancer elements.

3. The promoter according to claim 2, wherein said enhancer element comprises 4 tandem repeats of the nucleotide sequence of SEQ ID NO:1 or SEQ ID NO:2.

4. The promoter according to claim 1, further comprising a nucleotide sequence comprising a transcription initiation site and a TATA box located downstream of said enhancer element.

5. The promoter according to claim 4, wherein said nucleotide sequence comprising a transcription initiation site and a TATA box is the nucleotide sequence of SEQ ID NO:3.

6. The promoter according to claim 4, which further comprises a CAAT box operatively-linked between said enhancer element and said nucleotide sequence comprising a transcription initiation site and a TATA box.

7. The promoter according to claim 4, wherein said nucleotide sequence comprising a transcription initiation site and a TATA box is selected from the group consisting of the −90 to +8 fragment of the Cauliflower Mosaic Virus 35S gene, the −204 to +8 fragment of tomato rbcS-3A gene, the −287 to +29 fragment of the PR1a gene and the −195 to +32 fragment of the potato PI-II gene.

8. The promoter according to claim 6, wherein said nucleotide sequence comprising a transcription initiation site and a TATA box is selected from the group consisting of the −90 to +8 fragment of the Cauliflower Mosaic Virus 35S gene, the −204 to +8 fragment of the tomato rbcS-3A gene, the −287 to +29 fragment of the PR1a gene and the −195 to +32 fragment of the potato PI-II gene.

9. A plasmid comprising:

a recombinant promoter functional in plant cells comprising at least one enhancer element comprising the nucleotide sequence of SEQ ID NO:1 or SEQ ID NO:2, and a transcription terminator functional in plant cells.

10. A plasmid comprising:

a recombinant promoter functional in plant cells comprising at least one enhancer element comprising the nucleotide sequence of SEQ ID NO:1 or SEQ ID NO:2;

a structural gene under control of said promoter; and a transcription terminator functional in plant cells.

11. The plasmid pGbox10 or pGbox11.

12. A plasmid comprising in operable linkage:

the promoter of claim 6;

a structural gene; and a transcription terminator functional in plant cells.

13. A plant cell transformed with a structural gene of interest under the control of the promoter of claim 1.

14. A plant cell comprising the plasmid of claim 9.

15. A plant cell transformed with the plasmid of claim 12.

16. A plant transformed with a structural gene of interest under the control of the promoter of claim 1.

17. A plant comprising the plasmid of claim 9.

18. A method for expressing in plant cells a structural gene of interest, which comprises:

transforming plant cells with said structural gene of interest under control of the promoter of claim 1.

19. The method of claim 18, wherein said plant cells are part of a whole plant.

20. The method of claim 19, which further comprises the step of harvesting said whole plant.

21. The method of claim 18, wherein said plant cells are isolated from a plant.

22. A method for constructing a plasmid, which comprises:

connecting in 5' to 3' orientation:
the promoter of claim 1;
a structural gene of interest; and
a transcription terminator functional in plant cells.

* * * * *